United States Patent [19]

Badesha et al.

[11] Patent Number: 4,624,701

[45] Date of Patent: * Nov. 25, 1986

[54] COREDUCTION PROCESS FOR INCORPORATION OF HALOGENS INTO CHALCOGENS AND CHALCOGENIDE ALLOYS

[75] Inventors: Santokh S. Badesha, Pittsford; Thomas W. Smith, Penfield; Ihor W. Tarnawskyj, Rochester, all of N.Y.

[73] Assignee: Xerox Corporation, Stamford, Conn.

[*] Notice: The portion of the term of this patent subsequent to Nov. 27, 2001 has been disclaimed.

[21] Appl. No.: 765,747

[22] Filed: Aug. 15, 1985

[51] Int. Cl.$^4$ .............................................. C01B 19/02
[52] U.S. Cl. ................................. 75/0.5 A; 423/510
[58] Field of Search ..................... 423/510; 75/0.5 A

[56] References Cited

U.S. PATENT DOCUMENTS

| | | | |
|---|---|---|---|
| 2,378,824 | 6/1945 | Betterton et al. | 23/209 |
| 2,834,652 | 5/1958 | Hollander et al. | 23/209 |
| 3,954,951 | 5/1976 | Buckley | 423/510 |
| 4,460,408 | 7/1984 | Badesha et al. | 423/510 |
| 4,484,945 | 11/1984 | Badesha et al. | 75/0.5 A |

*Primary Examiner*—Peter D. Rosenberg
*Attorney, Agent, or Firm*—E. O. Palazzo

[57] ABSTRACT

A process for the preparation of halogenated chalcogens, or halogenated chalcogenide alloys which comprises providing in solution pure esters of the desired chalcogen, and subsequently subjecting a mixture of the esters and a chalcogenide halide to a coreduction reaction.

27 Claims, No Drawings

COREDUCTION PROCESS FOR INCORPORATION OF HALOGENS INTO CHALCOGENS AND CHALCOGENIDE ALLOYS

BACKGROUND OF THE INVENTION

This invention is generally directed to processes for the preparation of halogenated chalcogens and halogenated chalcogenide alloys. More specifically, the present invention is directed to the preparation of chalcogenide alloys, and chalcogens with halogens, such as chlorine contained therein, by simultaneously coreducing the appropriate corresponding esters, and the halogenated analogs thereof. Accordingly, there is provided in accordance with the present invention a simple, economically attractive, low temperature process for the direct chemical preparation of halogenated chalcogens, inclusive of selenium, by the coreduction reaction of a chalcogen ester, and a chalcogen halide. The resulting halogenated chalcogens, and further chalcogenide alloys prepared in accordance with the process of the present invention are useful as photoconductive imaging members that can be selected for electrostatic imaging processes. In contrast to prior art processes, in accordance with the process of the present invention the halogen is homogeneously incorporated into the chalcogens or chalcogenide alloys, as well as being covalently bonded thereto. Thus, for example, in accordance with the process of the present invention the halogens are incorporated as stable halogen chalcogen, or halogen chalcogenide bonds.

The incorporation of halogens into selenium or selenium alloys, and their application as xerographic imaging members is well known. These members can be subjected to a uniform electrostatic charge to permit the sensitization of the surface of the photoconductive layer, followed by imagewise exposure to activating electromagnetic radiation which selectively dissipates the charge in the illuminated areas of the photoconductive member, and wherein a latent electrostatic image is formed in the non-illuminated areas. The resulting image may then be developed and rendered visible by depositing thereon toner particles. The aforementioned commercially available halogenated selenium or selenium alloys are generally substantially pure, 99.99 percent or greater, since the presence of impurities has a tendency to adversely effect the imaging properties of selenium, including the electrical properties thereof, causing copy quality to be relatively poor in comparison to devices wherein high purity components are used.

Also, known are layered organic and inorganic photoresponsive devices with amorphous selenium, trigonal selenium, amorphous selenium alloys, or halogen doped selenium alloys. One such photoresponsive member is comprised of a substrate, a photogenerating layer of a metal phthalocyamine, a metal free phthalocyanine, vanadyl phthalocyanine, or selenium tellurium alloys, and a transport layer with an aryl diamine dispersed in a resinous binder, reference U.S. Pat. No. 4,265,990, the disclosure of which is totally incorporated herein by reference.

Further, many processes are known for the preparation of chalcogenide alloys, particularly selenium containing alloys including, for example, the melt blending of elemental substances, such as selenium and arsenic in the proportions desired in the final alloy product. Thus, for example, there is disclosed in U.S. Pat. No. 3,634,134 the preparation of arsenic-selenium alloys by mixing a master alloy with the appropriate proportions of arsenic and selenium. This method involves high temperatures, and in most instances, crystalline materials are not obtainable. Further, in some situations depending on the process parameters, there is generated with the melt blending process an inhomogeneous mixture of arsenic, selenium, and an arsenic selenium alloy. Additionally, in these processes, there must be selected for evaporation arsenic and selenium of a high purity, that is 99.99 percent; however, processes for obtaining these purities require undesirable high temperature distillations and costly equipment. A similar melt blending method for preparing selenium alloys is disclosed in U.S. Pat. No. 3,911,091. The alloys obtained may then be doped with halogens by, for example, a complex physical process wherein halogen gas is bubbled through the alloy melt.

Moreover, there is disclosed in U.S. Pat. No. 3,723,105 a process for preparing a selenium-tellurium alloy by heating a mixture of selenium and tellurium present in an amount of from 1 to 25 percent by weight to a temperature not lower than 350° C., followed by gradual cooling of the molten selenium and tellurium to about the melting point temperature of the selenium tellurium alloy at a rate not higher than 100° C. per hour; and subsequently quenching to room temperature within 10 minutes.

Additionally, there is disclosed in U.S. Pat. No. 4,121,981 the preparation of a selenium alloy by, for example, electrochemically codepositing selenium and tellurium onto a substrate from a solution of their ions wherein the relative amount of alloy deposited on the cathode is controlled by the concentrations of the selenium and the tellurium in the electrolyte, and by other electrochemical conditions. Once the selenium tellurium layer deposited on the cathode has reached the desired thickness, deposition is discontinued and the cathode is removed.

Also, there is disclosed in U.S. Pat. No. 3,524,745, the preparation of an arsenic antimony selenium alloy by heating a mixture of these materials at a temperature of 600° C. for a period of several hours in a vacuum, followed by air cooling to room temperature. According to the teachings of this patent, the cooled alloy depending on the initial composition is a mixture of crystalline and amorphous phases, or completely amorphous.

Furthermore, there is illustrated in U.S. Pat. No. 4,484,945, the disclosure of which is totally incorporated herein by reference, a process for the preparation of chalcogenide alloys in high purity which comprises providing a solution mixture of oxides of the desired chalcogens, and subsequently subjecting this mixture to a simultaneous coreduction reaction. Similarly, in U.S. Pat. No. 4,460,408, the disclosure of which is totally incorporated herein by reference, there is illustrated a process for the preparation of chalcogenide allows in high purity which comprises providing pure esters of the desired chalcogenide; and subsequently subjecting the mixture of esters to a coreduction reaction.

Although these processes, as well as others, are suitable for their intended purposes, in most instances, excluding the process described in the U.S. Pat. Nos. 4,484,945 and 4,460,408, high temperatures and distillation steps are needed to generate the product desired. Further, in some instances, these processes result in selenium alloys which have differing electrical properties which is believed to be a result of inhomogenities known to exist in noncrystalline glasses. Also, many of the prior art halogenated alloy processes involve a physical process rather than the advantageous chemical method.

There thus continues to be a need for new improved processes of preparing halogenated chalcogens, and chalcogenide alloys. Additionally, there continues to be a need for an improved simple, economically attractive, direct process for the preparation of high purity halogenated chalcogens, and halogenated chalcogenide alloys of high purity. Also, there is a need for improved processes wherein binary halogenated chalcogenide and ternary halogenated alloys can be obtained in high purity by the selection of substantially similar process parameters. Additionally, there continues to be a need for improved processes of preparing halogenated chalcogenide alloys that are homogeneous, are of a crystalline form, and that can be obtained in various proportions without high temperatures. These needs can be satisfied in accordance with the process of the present invention wherein, for example, substantially halogenated homogeneous chalcogenide crystalline alloys result by the coreduction of a mixture of a chalcogenide ester, and the corresponding halogenated analog.

SUMMARY OF THE INVENTION

It is an object of the present invention to provide improved processes for the preparation of halogenated chalcogens, and halogenated chalcogenide alloys which overcome some of the above-noted disadvantages.

It is yet another object of the present invention to provide improved processes for the preparation of halogenated high purity chalcogens, and chalcogenide alloys by simultaneously subjecting a mixture of the corresponding pure esters, and halogenated analogs, such as a chalcogenide halide, to a coreduction reaction.

Yet another specific object of the present invention is the provision of an improved process for the preparation of halogenated, especially chlorinated, alloys of selenium tellurium, selenium arsenic, selenium antimony, selenium bismuth, selenium-tellurium-arsenic, selenium arsenic bismuth, selenium tellurium antimony, selenium-tellurium-sulfur, and selenium-tellurium by the coreduction of a mixture of the corresponding pure esters thereof, and a halogenated chalcogenide or halogenated oxyhalide.

Also, in another object of the present invention there is provided processes for the preparation of halogenated chalcogens, and chalcogenide alloys, which process is simple, economically attractive, presents no significant environmental pollution problems, can be effected at low temperatures, and results in high product yields.

A further object of the present invention is the provision of improved processes for controlling the permanent incorporation of halogen into a chalcogen, or chalcogenide alloy by a chemical process.

Further, another object of the present invention is the provision of improved processes for homogeneously incorporating halogens into chalcogens and their corresponding alloys.

These and other objects of the present invention are accomplished by providing an improved process for the preparation of high purity halogenated chalcogens, and halogenated chalcogenide alloys, which comprises subjecting a mixture of the corresponding esters and halogenated analogs to a coreduction reaction. In one aspect, the process of the present invention comprises the formation of esters of the desired elements by treating the corresponding oxides with an alcohol or glycol, followed by subjecting a solution mixture of the resulting esters of high purity, and a halogenated chalcogenide to a coreduction reaction. Thus, the element oxides of Groups VA and VIA of the Periodic Table are contacted with an alcohol, or diol enabling the formation of an ester which is subsequently purified. Therefore, for example, the pure selenium ester can be obtained by the condensation reaction of selenium dioxide with an alcohol. The corresponding esters of other elements, such as arsenic, antimony, bismuth, and tellurium are usually formed by reacting the corresponding oxides with a glycol, or by the treatment of the oxides with an alcohol, and the corresponding alkoxides. Also, the selenium ester can be formulated by reacting the oxides of selenium, with an alcohol, and the corresponding alkoxide. Subsequently, the resulting esters are purified by distillation, recrystallization, and similar known purification methods. These esters are then formulated into a solution with a chalcogen oxyhalide, a chalcogenide halide, or a dihalogenide halide, and thereafter the resulting mixture is subjected to a coreduction reaction.

DESCRIPTION OF THE PREFERRED EMBODIMENTS

The process of the present invention involves subjecting a mixture of high purity chalcogen or chalcogenide esters, and their halogenated analogs, inclusive of chalcogen halides, to a simultaneous coreduction reaction enabling the generation of a chalcogen or an alloy with a halogen chemically bonded thereto. The preparation of the esters, which is described in U.S. Ser. No. 404,259, Aug. 2, 1982, entitled Process For Selenium Purification, the disclosure of which is totally incorporated herein by reference; and U.S. Pat. No. 4,530,718, the disclosure of which is totally incorporated herein by reference, comprises the reaction of the oxides of Groups VA to VIA of the Periodic Table, with an alcohol or a glycol. The resulting chalcogen ester and a chalcogen halide, or other similar reactant, are then subjected to a reduction reaction wit, for example hydrazine, sulfur dioxide, thioureas, or hydroxylamine.

The selenium ester $(RO)_2SeO$, selected for the process of the present invention wherein R is an alkyl group, is prepared as described in copending application U.S. Ser. No. 404,259, the disclosure of which has been totally incorporated herein by reference. In one method of preparation, selenious acid $H_2SeO_3$ is reacted with an alcohol ROH, wherein R is an alkyl group of from 1 carbon atom to about 30 carbon atoms, and preferably from 1 carbon atom to about 6 carbon atoms. Water resulting from this reaction can be optionally removed by an azeotropic distillation to yield the pure liquid diethyl selenite $(RO)_2SeO$ after vacuum distillation.

Illustrative examples of alcohols selected for obtaining the desired high purity selenium ester include those as described in the referenced copending application, U.S. Ser. No. 404,259, such as methanol, ethanol, propanol, butanol, pentanol, hexanol, and octanol. The preferred alcohols selected for forming the selenium ester include methanol, ethanol, and propanol.

The tellurium ester is formed in a similar manner, reference for example U.S. Pat. No. 4,389,389, the disclosure of which is totally incorporated herein by reference, wherein, for example, tellurium oxide is reacted with a cyclic aliphatic or aromatic diol of the formula $HO(R_n)OH$, wherein R is a cyclic aliphatic ring or an aromatic ring; or where tellurium oxide is reacted with an aliphatic diol of the formula $HO(CR_1R_2)_nOH$ wherein $R_1$ and $R_2$ are independently selected from the group consisting of hydrogen or alkyl groups of from 1 carbon atom to about 30 carbon atoms, and n is a number from 1 to about 10. This reaction generally involves the use of aromatic or aliphatic sulfonic acids, including p-toluene sulfonic acid catalysts. In one embodiment the process for preparing a pure tellurium ester comprises stirring and heating a mixture of tellurium oxide and a diol, in the presence of a catalyst for a period of time sufficient to permit a clear solution. Also, tetraalkoxytelluranes can be prepared by the condensation of tellurium tetrachloride with alkoxides, in the presence of certain alcohols, yielding, for example, an ester of the formula $(R_3O)_4Te$, wherein $R_3$ is an alkyl group.

Examples of aliphatic diols selected for reaction with the tellurium oxide are ethylene glycol, 1,2 or 1,3-propane diol, propylene glycol, butylene glycol, 1,2 1,3 or 1,4-butane diols, analogous hexane diols, and the like, with ethylene glycol being preferred. Aromatic diols that may be selected are catechol, and resorcinol.

The high purity arsenic ester can be prepared in a substantially similar manner; thus, for example the arsenic ester, bis(arsenic triglycollate) of the formula

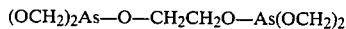
$(OCH_2)_2As-O-CH_2CH_2O-As(OCH_2)_2$ is formulated by treating arsenic oxide ($As_2O_3$) with ethylene glycol in the presence of a p-toluene sulfonic acid catalyst. Other arsenic esters may also be selected for the process of the present invention including arsenic alkoxides of the general formula $AS(OR)_3$ wherein R is as defined herein. The arsenic alkoxides are generally prepared by reacting arsenic trichloride with sodium alkoxides in the presence of the corresponding alcohols.

Similarly, the corresponding commercially available dialkyl sulfite ester can be prepared by the reaction of thionyl chloride with an alcohol. Thus, dimethyl sulfite can be generated by the condensation reaction of thionyl chloride with methanol. Other esters of the elements of the Periodic Table of Groups VA and VIA, which can be selected for the process of the present invention are generally prepared by the condensation of the corresponding oxides or chlorides with aliphatic and aromatic alcohols and diols.

Examples of the halogen source second reactant are chalcogenide halides, such as selenium tetrachloride, selenium tetrabromide, selenium tetraiodide, selenium tetrafluoride, tellurium tetrachloride, tellurium tetrafluroide, tellurium tetrabromide, arsenic tetrachloride, arsenic tetrabromide, and arsenic tetrafluoride; chalcogenide oxyhalides, inclusive of selenium oxychloride, selenium oxybromide, selenium oxyfluoride, tellurium oxychloride, and tellurium oxyfluoride; dichalcogenide halogens, like diselenium dichloride, and diselenium dibromide.

Thereafter, the reaction mixture comprised of the above illustrated chalcogen ester, and halogenated chalcogenide are subjected to a reduction reaction in an organic solvent, such as aliphatic alcohols including methanol and ethanol; cellosolve; and aliphatic glycols inclusive of ethylene glycol. By reduction in accordance with the process of the present invention is meant that the reactants are simultaneously reduced by optionally dissolving them in a suitable organic solvent, followed by the addition of a common reducing agent. Examples of reducing agents that may be selected include sulfur dioxide, hydrazine, thioureas, and hydroxylamine, with hydrazine being preferred. Thus, in one illustrative reduction sequence, the hydrazine is added dropwise to the reaction mixture until conversion to the halogenated chalcogens, or chalcogenide alloys is completed as evidenced by, for example, cessation of bubbling or emission of nitrogen gas.

The resulting halogenated chalcogenide or halogenated chalcogen can be filtered from the reaction mixture, washed with suitable solvents such as water or cellosolve, providing products of 99.99 percent purity with, for example, from about 10 to about 6,000 parts per million of halogen chemically incorporated therein.

More specifically, the reduction reactions are accomplished as described in the copending application and U.S. patents identified herein, the disclosure of each being previously incorporated herein by reference. Thus, the reduction reaction can be accomplished at various suitable temperatures dependent on, for example, the reducing agent selected and the solvent used. Generally, the reduction is accomplished at a relatively low temperature not exceeding, for example, about 100° C. Specifically, the reduction reaction temperature can be from about 25° C. to about 100° C. depending on the reducing agent and the solvent being employed.

The amount of reducing agent needed is dependent on a number of factors, such as its chemical composition, reaction temperatures, concentration of reactants employed, and the like. Thus, for example, hydrazine is usually added in an equimolar quantity until completion of the reduction reaction, while sulfur dioxide is generally bubbled through the solution of the esters selected for a period of time to cause complete precipitation of the product.

There can thus be formulated in accordance with the process of the present invention chalcogens, especially selenium, and chalcogenide alloys, with chlorine chemically incorporated therein in an amount of, for example, from about 10 to about 10,000 parts per million; and more specifically in the amounts 58, 87, 89, 107, 109, 110, 132, 146, 148, 154, 213, 355, 506, 604, 650, 703, 1770, 1800, 1930, 2090, 2100, 4164 and 4200 parts per million. The composition of these products can be determined by Optical Emission Spectroscopy, while the chlorine contents were determined by polarography.

Chalcogenide alloys can be prepared in accordance with the process of the present invention by affecting a coreduction of a mixture of the appropriate corresponding esters and a chalcogenide halide second reaction. Specifically, an alloy with about 90 percent by weight of selenium, and 10 percent by weight of tellurium; and having incorporated therein from about 10 to about 10,000 parts per million of halogen can be prepared by the simultaneous coreduction of about 9 moles of a selenium ester, about 1 mole of a tellurium ester, and about 2 moles of selenium tetrachloride. Other selenium alloys, inclusive of selenium arsenic, with 0.5 percent by weight of arsenic and about 100 to 300 parts per million of chlorine, can be prepared in a similar manner.

The halogenated alloys and other products prepared in accordance with the process of the present invention can be formulated into imaging members by, for example, depositing them on a suitable conductive substrate such as aluminum. The resulting photoconductive member can then be incorporated into an electrostatographic imaging process wherein the member is charged to a suitable polarity, followed by development with a toner composition comprised of resin particles and pigment particles, thereafter transferring the developed image to a suitable substrate, and optionally permanently affixing the image thereto. Furthermore, the products prepared in accordance with the process of the present invention can be utilized in layered photoresponsive devices as the generating composition. These devices usually consist of a conductive substrate, a generating layer, and a transport layer, reference U.S. Pat. No. 4,265,990, the disclosure of which is totally incorporated herein by reference.

The following examples specifically defining preferred embodiments of the present invention are now provided, which examples are not intended to limit the scope of the present invention, it being noted that various alternative parameters which are not specifically mentioned are included within the scope of the present invention. Parts and percentages are by weight unless otherwise indicated.

EXAMPLE I

This example describes the preparation of tetraalkoxytellurane by the condensation of tellurium dioxide with ethylene glycol.

A mixture of commercial grade tellurium dioxide 160 grams, p-toluenesulfonic acid 5 grams, and ethylene glycol 1600 milliliters were charged into a 2-liter round bottom flask equipped with a reflux condenser. The contents of the flask were heated and stirred under an argon atmosphere at 120° C. for 3 hours, and then at 160° C. until a clear solution was obtained. This solution was then cooled to room temperature, and allowed to remain on a bench for 5 hours, resulting in the formation of a precipitate of white needles. This precipitate was separated from the mixture by filtration, washed with 100 milliliters (2×50 milliliters) of cellosolve. These white needles were further purified by recrystallization from a cellosolve solution. The resultant solid, obtained in 86 percent yield, was identified as the tellurium ester tetraalkoxytellurane by known spectroscopic and analytical techniques.

An additional amount of tetraalkoxytellurane can be obtained by concentrating the filtrate resulting from the above separation processes.

EXAMPLE II

This example describes the conversion of selenium dioxide into dimethyl selenite.

A mixture of selenium dioxide, 50 grams, p-toluene sulfonic acid, 5 grams in 500 milliliters of methanol, was charged to a 1-liter round bottom flask fitted with a Dean-Stark apparatus. The reaction mixture was refluxed and stirred on a magnetic stirrer for 5 hours during which time a clear solution results. Chloroform, 200 milliliters, was then added to the reaction flask and water removed azeotropically This reaction was completed in approximately 6 hours. Excess methanol and chloroform were removed by distillation and the residue remaining in the flask was distilled under high vacuum. Pure dimethyl selenite, 60 grams, 85 percent yield, which distills at 43° C., 5 millimeters of mercurcy was collected, and identified by spectroscopic and analytical analysis.

EXAMPLE III

This example describes the preparation of bis(arsenic triglycollate) by the condensation of arsenic (III) oxide with ethylene glycol.

A mixture of aresenic (III) oxide 10 grams, p-toluene sulfonic acid 0.1 grams and ethylene glycol 30 milliliters was charged to a 100 milliliter round bottom flask fitted with a reflux condenser. The mixture was stirred at 65° C. on a magnetic stirrer under argon atmosphere. A clear solution was obtained in approximately one hour. The resulting solution was then subjected to a high vacuum distillation and the fraction distilling at 140°–145° C., 0.5 millimeters of mercury was collected. The resulting pure clear liquid, 95 grams, 57 percent yield was identified as bis(arsenic triglycollate) by spectroscopic and analytical analysis.

EXAMPLE IV

There was prepared a selenium chlorine product by adding to a 250 milliliter Erlenmeyer flask a solution of 10 grams of diethyl selenite obtained from Example II, and 2 grams of selenium oxychloride in 50 milliliters of ethanol. This solution was stirred and warmed to slightly above room temperature. Thereafter, a solution of 4 milliliters of hydrazine and 20 milliliters of ethanol was added dropwise to the reaction flask. An exothermic reaction occurred and nitrogen gas was evolved therefrom. Completion of the reduction reaction was indicated by the cessation of nitrogen gas from the reaction mixture. Thereafter, and subsequent to filtration, there was obtained a black precipitate. The precipitate was washed with hot water yielding a total of 4.9 grams of a selenium product with 650 parts per million of chlorine as determined by differential-pulse polarographic analysis.

EXAMPLE V

There were prepared 4 different selenium chlorine products by repeating the procedure of Example I with the exception that there was selected 1.03 grams, 0.52 grams, 0.253 grams and 0.114 grams, respectively, of selenium oxychloride in place of the 2 grams of selenium oxychloride. There resulted selenium products, 4.4 grams, with 355 parts per million of chlorine incorporated therein; 4.1 grams with 213 parts per million of chlorine incorporated therein; 3.95 grams with 132 parts per million of chlorine incorporated therein; and 4.81 grams with 58 parts per million of chlorine incorporated therein as determined by differential-pulse polarographic analysis.

The halogenated selenium products prepared in accordance with the above processes are then formulated into four imaging members by the vapor deposition of the respective compositions in a thickness of about 50–60 microns on an aluminum substrate with a thickness of about 2,000 to 3,000 microns. These devices were then incorporated into an electrostatographic imaging apparatus wherein a positive latent electrostatic latent image is formed on the photoconductive device. The images are then developed with a toner composition comprised of a styrene n-butylmethacrylate copolymer resin, 90 percent by weight, and 10 percent by weight of carbon black. There can be obtained in each instance excellent quality images of high resolution, no background deposits, for over 1,000 copying cycles.

EXAMPLE VI

Preparation of selenium chlorine product with sulfur dioxide as a reducing agent.

In a 2-liter Erlenmeyer flask a solution of 17.8 grams of selenium oxychloride and 89.2 grams of diethyl selenite in 600 milliliters of ethanol was prepared by stirring and heating. Thereafter, sulfur dioxide was vigorously bubbled through the above solution while heating and stirring was continued. The bubbling was continued for 4 hours after which time the resulting black precipitate was filtered, and washed 4 times with 50 milliliters of hot water. There was collected 46 grams of chlorinated selenium with 4,164 parts per million of chlorine as determined by differential-pulse polarography.

Other modifications of the present invention will occur to those skilled in the art based upon a reading of the disclosure of the present application and these modifications are intended to be included within the scope of the present invention.

What is claimed is:

1. A process for the preparation of components selected from the group consisting of halogenated chalcogens, and halogenated chalcogenide alloys which comprises providing in solution pure esters of the desired chalcogen, and subsequently subjecting a mixture of the esters and a chalcogenide halide to a coreduction reaction.

2. A process in accordance with claim 1, wherein the pure esters are comprised of selenium and tellurium.

3. A process in accordance with claim 1, wherein the pure esters are comprised of selenium and arsenic.

4. A process in accordance with claim 1, wherein the chalcogen reactant is a selenium ester.

5. A process in accordance with claim 1, wherein the chalcogen reactant is an arsenic ester.

6. A process in accordance with claim 1, wherein there is selected as the ester reactant a selenium ester of the formula $(RO)_2SeO$, a tellurium ester of the formula $(RO)_4Te$, an arsenic ester of the formula $(OCH_2)AS—CH_2CH_2O\ As(OCH_2)_2$, or a sulfur ester of the formula $(RO)_2SO$, wherein R is an alkyl group.

7. A process in accordance with claim 1, wherein the reducing agent is hydrazine.

8. A process in accordance with claim 1, wherein the reducing agent is sulfur dioxide.

9. A process in accordance with claim 1, wherein the chalcogenide halide is a selenium tetrahalide.

10. A process in accordance with claim 1, wherein the chalcogenide halide is a selenium tetrachloride.

11. A process in accordance with claim 1, wherein the chalcogenide halide is a selenium oxyhalide.

12. A process in accordance with claim 1, wherein the chalcogenide halide is a selenium oxychloride.

13. A process in accordance with claim 1, wherein the chalcogenide halide is a diselenium dichloride.

14. A process in accordance with claim 1, wherein the chalcogenide halide is a tellurium tetrahalide.

15. A process in accordance with claim 1, wherein the chalcogenide halide is ditellurium dichloride.

16. A process in accordance with claim 1, wherein the results of a selenium arsenic alloy with from about 1 part per million to 10,000 parts per million of chlorine.

17. A process in accordance with claim 1, wherein there results a selenium tellurium arsenic alloy with from about 1 part per million to 10,000 parts per million of chlorine.

18. A process in accordance with claim 1, wherein there results a selenium sulfur alloy with from about 1 part per million to 10,000 parts per million of chlorine.

19. A process in accordance with claim 1, wherein there results selenium with from about 1 part per million to 6,000 parts per million of chlorine.

20. A process in accordance with claim 1, wherein an alcohol is selected for the formation of the solution.

21. A process in accordance with claim 1, wherein the reduction reaction is accomplished at a temperature of from about 25° C. to about 100° C.

22. A process in accordance with claim 1 wherein there is formulated a selenium tellurium alloy with from about 1 part per million to about 10,000 parts per million of chlorine.

23. A process in accordance with claim 22 wherein selenium is present in an amount of about 90 percent by weight, and tellurium is present in an amount of about 10 percent by weight.

24. A process in accordance with claim 22 wherein selenium is present in an amount of 75 percent by weight, and tellurium is present in an amount of 25 percent by weight.

25. A process in accordance with claim 1 wherein there is formulated a selenium arsenic alloy with from about 500 parts per million to about 5,000 parts per million of chlorine.

26. A process in accordance with claim 25 wherein selenium is present in an amount of 95.5 percent, and arsenic is present in an amount of 0.5 percent.

27. A process for affecting the preparation of components selected from the group consisting of halogenated chalcogens, and halogenated chalcogenide alloys consisting essentially of providing in solution pure esters of the desired chalcogen, and subsequently subjecting a mixture of the esters and a chalcogenide halide to a coreduction reaction.

* * * * *